United States Patent
Nakazawa et al.

(10) Patent No.: US 9,217,123 B2
(45) Date of Patent: Dec. 22, 2015

(54) 13-METHYL-9-CYCLOPENTADECEN-15-OLIDE

(71) Applicant: Kao Corporation, Chuo-ku (JP)

(72) Inventors: Yuki Nakazawa, Wakayama (JP); Takashi Aoki, Wakayama (JP); Tsuyoshi Toyabe, Funabashi (JP)

(73) Assignee: Kao Corporation, Chuo-ku (JP)

( * ) Notice: Subject to any disclaimer, the term of this patent is extended or adjusted under 35 U.S.C. 154(b) by 52 days.

(21) Appl. No.: 14/219,486

(22) Filed: Mar. 19, 2014

(65) Prior Publication Data

US 2014/0287971 A1   Sep. 25, 2014

(30) Foreign Application Priority Data

Mar. 19, 2013 (JP) ................................. 2013-056934

(51) Int. Cl.
*A61K 8/00* (2006.01)
*C11B 9/00* (2006.01)
*C07D 315/00* (2006.01)
*C11D 3/50* (2006.01)

(52) U.S. Cl.
CPC ............ *C11B 9/0084* (2013.01); *C07D 315/00* (2013.01); *C11D 3/50* (2013.01)

(58) Field of Classification Search
CPC ... C07D 313/00; C11B 9/0024; C11B 9/0084
See application file for complete search history.

(56) References Cited

U.S. PATENT DOCUMENTS

| 6,255,276 B1 | 7/2001 | Frater et al. |
| 2008/0020963 A1 | 1/2008 | Takaoka |
| 2011/0269664 A1 | 11/2011 | Takahashi et al. |

FOREIGN PATENT DOCUMENTS

| EP | 0 841 333 A1 | 5/1998 |
| EP | 1 741 706 A1 | 1/2007 |
| EP | 2781515 | * 9/2014 |
| JP | 11-193395 | 7/1999 |
| JP | 2000-053675 | 2/2000 |
| JP | 2005-179601 | 7/2005 |
| JP | 2010-163366 | 7/2010 |
| WO | 2005/105773 | 11/2005 |

OTHER PUBLICATIONS

Extended European Search Report issued Apr. 16, 2014 in Patent Application No. 14160534.5.
Genichi Indo et al., "Synthetic Perfumes, Chemistry and Commodity Knowledge", Enlarged and Revised Edition, 2005, pp. 391-403 with partial machine translation.

* cited by examiner

*Primary Examiner* — John Hardee
(74) *Attorney, Agent, or Firm* — Oblon, McClelland, Maier & Neustadt, L.L.P.

(57) ABSTRACT

It is intended to provide a compound and a fragrance composition containing the same, wherein the compound has an odor with a tone of musk and a side note of woody tone, which are useful as fragrances, is excellent in fragrance retention, and can be blended with another fragrance to emphasize the top note and to enhance the feeling of cleanliness and refreshingness. It also is intended to provide 13-Methyl-9-cyclopentadecen-15-olide and a fragrance composition containing 13-methyl-9-cyclopentadecen-15-olide.

17 Claims, No Drawings

13-METHYL-9-CYCLOPENTADECEN-15-OLIDE

FIELD OF THE INVENTION

The present invention relates to 13-methyl-9-cyclopentadecen-15-olide and a fragrance composition containing the same.

BACKGROUND OF THE INVENTION

Fragrance is an important element that creates, for example, preference, a sense of luxury, a sense of ease, and expectations for the effect for products and the like. Furthermore, a distinctive fragrance provides a product differentiation effect and the capacity for attracting customers. On the other hand, in order to control, for example, a long-lasting property and balance of fragrance, generally, a fragrance is imparted to a product using a fragrance composition in which a plurality of fragrance materials are mixed together. It is required for the fragrance materials composing the fragrance composition to be highly harmonious with other fragrance materials.

Particularly, natural musks have been used as expensive fragrances since ancient times. Among them, some lactone compounds are synthesized as macrocyclic musks.

For example, cyclopentadecanolide has an elegant, sweet, and musk-like odor, ambrettolide has an elegant musk-like odor, Habanolide exhibits a very elegant musk-like odor, and cyclohexadecanolide has a musk odor (Non-Patent Document 1).

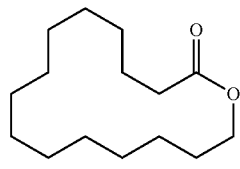

Cyclopentadecanolide

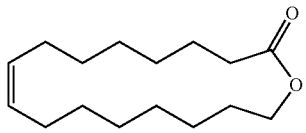

Ambrettolide

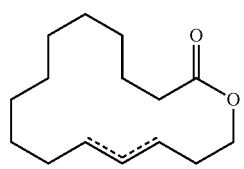

Habanolide

In addition, Patent Document 1 describes that 11-methyl-13-cyclotridecanolide, 12-methyl-14-cyclotetradecanolide, and 13-methyl-15-cyclopentadecanolide each have a strong musk odor with an excellent long-lasting property.

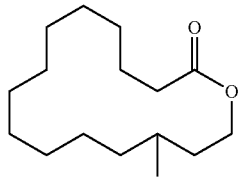

13-Methyl-15-cyclo
pentadecanolide

Patent Document 2 discloses a method of producing a macrocyclic lactone compound with a double bond, wherein a specific ester compound is cyclized by a metathesis reaction for the purpose of obtaining a macrocyclic lactone compound that has an excellent odor quality, a powdery feeling, and a musk-like odor.

Patent Document 3 describes that a macrocyclic lactone compound with a specific alkyl group has an excellent musk-like odor and can be produced easily.

Patent Document 4 discloses an odorizing composition containing a specific compound having a strong musk odor such as oxacycloheptadec-12-en-2-one or a mixture thereof, excluding a specific compound such as Z-oxacyclopentadaca-6-en-2-one as the compound.

Very roughly speaking, fragrance materials have similar fragrance notes when they have similar structures to each other, but there are many exceptions. Particularly, when a plurality of substituents are combined to change the fragrance note, it is difficult to predict how the fragrance note will change and it also is difficult to predict the harmonicity with other fragrance materials.

PRIOR ART DOCUMENTS

Non-Patent Document

[Non-Patent Document 1] "Gosei Koryo, Kagaku to Shohin Chishiki" (Synthetic Perfumes, Chemistry and Commodity Knowledge), authored by Genichi Indo, Enlarged and Revised Edition, 2005, pp. 391-403

Patent Documents

[Patent Document 1] WO2005/105773
[Patent Document 2] JP 2000-53675 A
[Patent Document 3] JP 2010-163366 A
[Patent Document 4] JP 11 (1999)-193395 A

SUMMARY OF THE INVENTION

Therefore, with the foregoing in mind, it is an object of the present invention to provide 13-methyl-9-cyclopentadecen-15-olide.

DETAILED DESCRIPTION OF THE INVENTION

The present invention is intended to provide a compound and a fragrance composition containing the same, wherein the compound has an odor with a tone of musk and a side note of woody tone, which are useful as fragrances, is excellent in fragrance retention, and can be blended with another fragrance to emphasize the top note and to enhance the feeling of cleanliness and refreshingness.

The present inventors have found that 13-methyl-9-cyclopentadecen-15-olide has an odor with a tone of musk and a side note of woody tone, is excellent in fragrance retention, and can be blended with another fragrance to emphasize the top note and to enhance the feeling of cleanliness and refreshingness, which allowed the present invention to be completed.

In other words, the present invention provides 13-methyl-9-cyclopentadecen-15-olide.

Furthermore, the present invention provides a fragrance composition containing 13-methyl-9-cyclopentadecen-15-olide.

13-Methyl-9-cyclopentadecen-15-olide of the present invention has an odor with a tone of musk and a side note of woody tone, which are useful as fragrances, is excellent in fragrance retention, and can be blended with another fragrance to emphasize the top note and to enhance the feeling of cleanliness and refreshingness.

The present invention provides 13-methyl-9-cyclopentadecen-15-olide. In the specification of the present application, the bonds represented by wavy lines in the formulae each indicate a cis form or a trans form or a mixture of a cis form and a trans form.

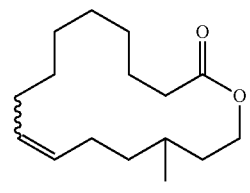

13-Methyl-9-cyclo pentadecen-15-olide

Methyl-9-cyclopentadecen-15-olide

13-Methyl-9-cyclopentadecen-15-olide of the present invention can be a racemate, a mixture of optically active R-form and S-form that exist in different ratios, or a R-form alone or a S-form alone, and preferably an optically active S-form alone. Specifically, the R-form is (R)-13-methyl-9-cyclopentadecen-15-olide and the S-form is (S)-13-methyl-9-cyclopentadecen-15-olide. Particularly, from the viewpoints of enhancing the odor with a woody tone and the refreshing feeling, it is preferable that the excess S-form rate be 0% or higher, more preferably at least 50%, further preferably at least 95%, and still further preferably 100%.

R-form and S-form of 13-methyl-9-cyclopentadecen-15-olide

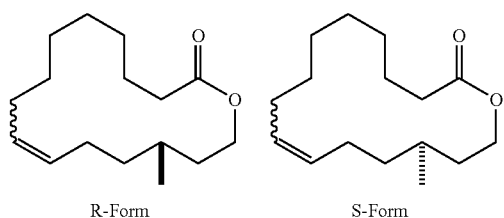

R-Form        S-Form

Method of Producing
13-Methyl-9-Cyclopentadecen-15-Olide

13-Methyl-9-cyclopentadecen-15-olide of the present invention can be synthesized utilizing a common organic chemical reaction and the method of producing it is not limited. A preferred method of producing 13-methyl-9-cyclopentadecen-15-olide of the present invention includes, for example, a step of cyclizing 3,7-dimethyl-6-octenyl-9-decenoate by a metathesis reaction.

<Step of Cyclizing by Metathesis Reaction>

This step is a step of cyclizing 3,7-dimethyl-6-octenyl-9-decenoate by a metathesis reaction.

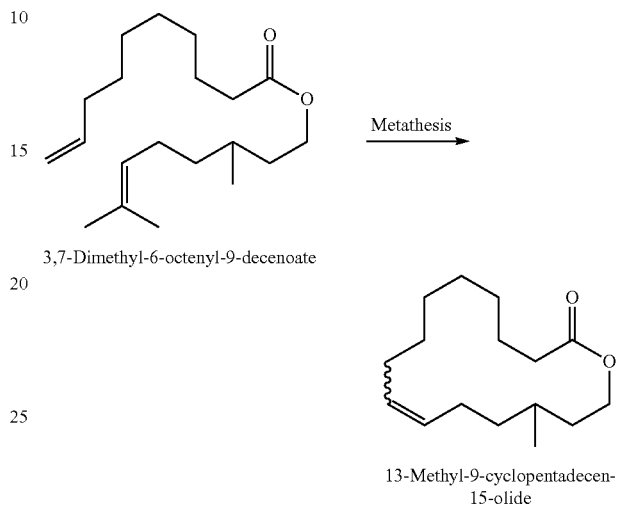

In this step, a catalyst is used. Examples of the catalyst to be used include a rhenium catalyst, a tungsten catalyst, a molybdenum catalyst, and a ruthenium catalyst. From the viewpoint of increasing the yield, the catalyst is preferably a ruthenium catalyst, particularly further preferably a ruthenium catalyst with a carbene ligand. As described above, the bond represented by a wavy line in the formula indicates a cis form or a trans form or a mixture of a cis form and a trans form. Cis form of 3,7-dimethyl-6-octenyl-9-decenoate alone or trans form of 3,7-dimethyl-6-octenyl-9-decenoate alone can be produced by using a suitable catalyst for each form.

When the ruthenium catalyst is used, the amount thereof is preferably at least 0.1 mol %, more preferably at least 1 mol % from the viewpoint of completing the reaction efficiently, and preferably 20 mol % or less, more preferably 10 mol % or less, and further preferably 5 mol % or less from an economic perspective and the viewpoint of facilitating its removal after the reaction.

The ruthenium catalyst with a carbene ligand is preferably a Grubbs catalyst represented by Formula (X) from the viewpoint of allowing the metathesis reaction to proceed efficiently.

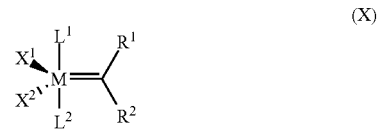
(X)

In Formula (X), M is Ru. $X^1$ and $X^2$ each are an anionic ligand. $X^1$ and $X^2$ may be identical to or different from each other. $R^1$ and $R^2$ each are H or a hydrocarbon group having 1 to 20 carbon atoms that may have a substituent. $R^1$ and $R^2$ may be identical to or different from each other. Alternatively, $R^1$ and $R^2$ may be combined together to form a ring structure. $L^1$ and $L^2$ each are a neutral ligand. $L^1$ and $L^2$ may be identical to or different from each other. Alternatively, either one of L¹ and L², either one of R¹ and R², and M may be combined together to form a ring structure.

From the viewpoint of increasing the yield, the anionic ligand of each of X¹ and X² is preferably halogen, more preferably Cl (chlorine).

From the viewpoint of increasing the yield, the ligand of either one of L¹ and L² is preferably phosphine or N-heterocyclic carbene. The phosphine is preferably trialkylphosphine, more preferably tricyclohexylphosphine. The N-heterocyclic carbene is preferably a pyridinium group or a group represented by Formula (Y), more preferably a group represented by Formula (Y).

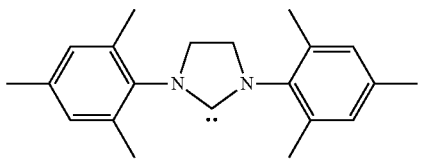

(Y)

R¹ and R² may be combined together to form a ring or may not be combined together to form a ring. From the viewpoint of increasing the yield, it is preferable that R¹ and R² be combined together to form a ring.

When R¹ and R² are combined together to form a ring structure, the ring structure is preferably 3-phenyl-1H-indene-1-ylidene from the viewpoint of increasing the yield.

Specific examples of the catalyst represented by Formula (X) include those with the structures described in Chem. Rev. 2009, 109, 3783.

From the viewpoints of increasing the yield and an economic efficiency, (X) is preferably a Grubbs catalyst represented by one of Formulae (X1) to (X9) below. In the formulae, PCy₃ denotes tricyclohexylphosphine, Mes denotes a 2,4,6-trimethylphenyl group, and $^i$Pr denotes an isopropyl group.

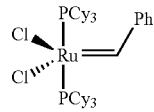

(X1)

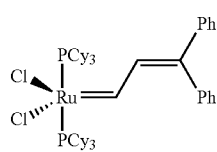

(X2)

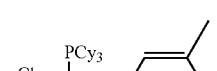

(X3)

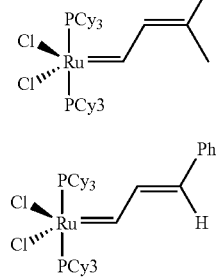

(X4)

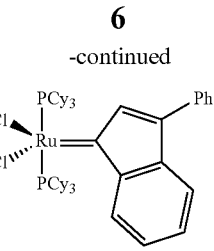

(X5)

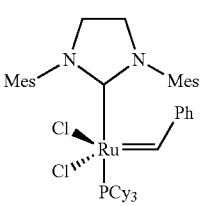

(X6)

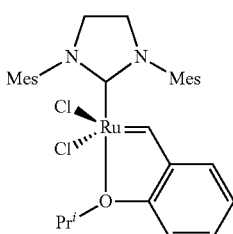

(X7)

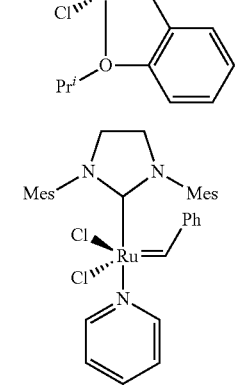

(X8)

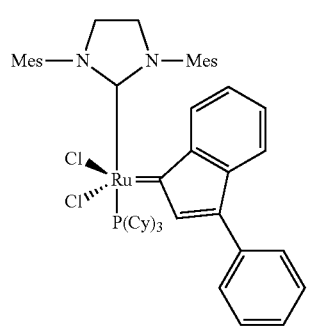

(X9)

Among them, from the viewpoint of economic efficiency, the Grubbs catalysts represented by Formulae (X1) to (X5) and (X9) are preferable and the Grubbs catalyst represented by Formula (X9) is more preferable.

Furthermore, the solvent to be used in this step is preferably an inactive solvent that is not involved in the reaction, more preferably a chlorine-based solvent or an aromatic solvent. A preferable chlorine-based solvent is dichloromethane. A preferable aromatic solvent is toluene. The concentration of 3,7-dimethyl-6-octenyl-9-decenoate, which is a reaction solution of this step in the case of using a solvent, is preferably at least 0.001 mol/L from the viewpoint of productivity, and preferably 0.01 mol/L or lower from the viewpoint of inhibiting the yield reduction caused by an intermolecular reaction.

The reaction temperature is preferably 5 to 50° C. and more preferably 40 to 50° C. from the viewpoint of completing the reaction efficiently. In the case of using a solvent having a boiling point in this range, it is preferable that the reaction be carried out under reflux. The reaction time is preferably 4 to 10 hours.

After completion of the reaction, it is preferable that purification such as removal of the catalyst be carried out using a method such as column chromatography. Specifically, it is more preferable that the purification be carried out by distillation from the viewpoint of improving the quality into a more preferable quality as a fragrance.

Preferably, 3,7-dimethyl-6-octenyl-9-decenoate is obtained by dehydration condensation of 3,7-dimethyl-6-octene-1-ol and 9-decenoic acid. That is, it is preferable that a suitable method of producing 13-methyl-9-cyclopentadecen-15-olide of the present invention further include a step of obtaining 3,7-dimethyl-6-octenyl-9-decenoate by dehydration condensation of 3,7-dimethyl-6-octene-1-ol and 9-decenoic acid.

<Step of Dehydration Condensation>

This step is a step of obtaining 3,7-dimethyl-6-octenyl-9-decenoate by dehydration condensation of 3,7-dimethyl-6-octene-1-ol and 9-decenoic acid.

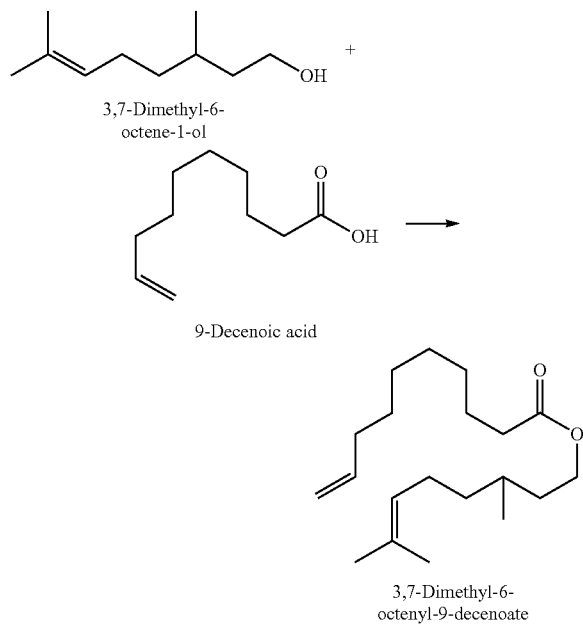

In this context, 3,7-dimethyl-6-octene-1-ol can be produced according to known documents. For example, it can be obtained by a method including fractional distillation and purification from, for example, a citronella oil, or a method including synthesis using, for example, alpha-pinene as a starting material.

Examples of available commercial products include (±)-Citronellol (Trade Name) manufactured by Wako Pure Chemical Industries, Ltd. In order to obtain an optically active substance of 13-methyl-9-cyclopentadecen-15-olide, for example, an optically active substance of 3,7-dimethyl-6-octene-1-ol such as (R)-(+)-3,7-dimethyl-6-octene-1-ol or (S)-(−)-3,7-dimethyl-6-octene-1-ol can be used. Preferably, (S)-(−)-3,7-dimethyl-6-octene-1-ol is used from the viewpoints of enhancing the side note of woody tone and the refreshing feeling.

Examples of commercial products of the optically active substance of 3,7-dimethyl-6-octene-1-ol include (R)-(+)-citronellol and (S)-(−)-citronellol (Trade Name) manufactured by SIGMA-ALDRICH.

9-Decenoic acid can be produced according to known documents. For example, it can be obtained by a method including synthesis using, for example, 1,10-decanediol as a starting material. Examples of commercial products thereof include 9-Decenoic Acid (Trade Name) manufactured by SIGMA-ALDRICH.

This step is carried out preferably by a method of azeotropic dehydration in the presence of acid catalyst using a solvent such as toluene or a method of stirring in the presence of a dehydrating agent, and more preferably by a method of stirring in the presence of a dehydrating agent from the viewpoint of inhibiting side reactions such as double bond isomerization.

The dehydrating agent is preferably carbodiimides, more preferably N,N'-dicyclohexylcarbodiimide or 1-ethyl-3-(3-dimethylaminopropyl)carbodiimide hydrochloride, and further preferably 1-ethyl-3-(3-dimethylaminopropyl)carbodiimide hydrochloride from the viewpoint of facilitating its removal after the reaction.

The amount of the dehydrating agent to be used is preferably at least 100 mol % with respect to 9-decenoic acid from the viewpoint of increasing the yield and preferably 150 mol % or less from an economic perspective. Furthermore, the amount of the dehydrating agent to be used is preferably at least 100 mol % with respect to 3,7-dimethyl-6-octene-1-ol from the viewpoint of increasing the yield and preferably 150 mol % or less from an economic perspective.

This step is carried out preferably in the presence of a reaction accelerator from the viewpoint of increasing the reaction rate. The reaction accelerator is preferably tertiary amines, more preferably pyridines from the viewpoint of allowing the reaction to proceed efficiently, and further preferably N,N'-dimethylaminopyridine. The amount of the reaction accelerator to be used is preferably at least 1 mol % with respect to 3,7-dimethyl-6-octene-1-ol from the viewpoint of allowing the reaction to proceed efficiently and preferably 20 mol % or less with respect to 3,7-dimethyl-6-octene-1-ol from an economic perspective.

The solvent to be used in this step is preferably an inactive solvent that is not involved in the reaction, more preferably particularly a chlorine-based solvent, and further preferably dichloromethane or chloroform.

The reaction temperature is preferably 5 to 50° C. and the reaction time is preferably 2 to 5 hours.

The 3,7-dimethyl-6-octenyl-9-decenoate obtained in this step can be used for the subsequent reaction without further being processed. However, it is preferable that it be used after impurities and the like originating from the starting materials are removed by, for example, liquid separation or column chromatography.

[Fragrance Composition]

The fragrance composition of the present invention contains 13-methyl-9-cyclopentadecen-15-olide. The amount of 13-methyl-9-cyclopentadecen-15-olide contained in the fragrance composition is preferably 0.01 to 99 mass %, more preferably 0.1 to 15 mass %, and further preferably 0.3 to 3 mass %. When 0.01 to 99 mass % of 13-methyl-9-cyclopentadecen-15-olide is contained, the top note can be emphasized and the feeling of cleanliness and refreshingness can be enhanced in the fragrance composition.

Since the fragrance composition of the present invention contains 13-methyl-9-cyclopentadecen-15-olide, it has an odor with a tone of musk and a side note of woody tone, is excellent in fragrance retention, and can be blended with another fragrance to emphasize the top note and to enhance the feeling of cleanliness and refreshingness. Furthermore, the fragrance composition of the present invention can contain, in addition to 13-methyl-9-cyclopentadecen-15-olide, another fragrance component that is commonly used or a blended fragrance with a desired composition as another fragrance and thereby it can be provided with an odor such as a citrus tone, a floral tone, a fruity tone, a herbal tone, a spicy tone, a green tone, a woody tone, a balsam tone, etc.

Another fragrance that can be combined with 13-methyl-9-cyclopentadecen-15-olide to be used in the fragrance composition of the present invention is preferably at least one selected from hydrocarbons, alcohols, phenols, aldehydes, ketones, acetals, ethers, esters, carbonates, lactones, oximes, nitriles, Schiff bases, natural essential oils, and natural extracts, particularly more preferably at least one selected from alcohols, aldehydes, ketones, ethers, esters, carbonates, natural essential oils, and natural extracts.

Examples of hydrocarbons include limonene, α-pinene, β-pinene, terpinene, p-cymene, cedrene, longifolene, valencene, camphene, and myrcene.

Examples of alcohols include aliphatic alcohols, terpene-based alcohols, and aromatic alcohols.

Examples of aliphatic alcohols include prenol, trans-2-hexenol, cis-3-hexenol, 2,6-dimethylheptanol, 1-octen-3-ol, 3,6-nonadiene-1-ol, Undecavertol (Trade Name of Givaudan, 4-methyl-3-decene-5-ol), 2,4-dimethyl-3-cyclohexene-1-methanol, isocyclogeraniol, 2-tert-butylcyclohexanol, 4-tert-butylcyclohexanol, Mayol (Trade Name of Firmenich, 4-(1-methylethyl)-cyclohexanemethanol), Amber Core (Trade Name of Kao Corporation), Timberol (Trade Name of Symrise, 1-(2,2,6-trimethylcyclohexyl)hexan-3-ol), Sandalmysore Core (Trade Name of Kao Corporation, 2-methyl-4-(2,2,3-trimethyl-3-cyclopenten-1-yl)-2-buten-1-ol), Bacdanol (Trade Name of IFF, 2-ethyl-4-(2,2,3-trimethyl-3-cyclopenten-1-yl)-2-buten-1-ol), and Florosa (Trade Name of Givaudan, 4-methyl-2-(2-methylpropyl)tetrahydro-2H-4-pyranol). Among them, Amber Core is preferable from the viewpoint of enhancing the feeling of cleanliness and refreshingness by being blended with another fragrance.

Examples of terpene-based alcohols include citronellol, hydroxycitronellol, linalool, dihydrolinalool, tetrahydrolinalool, ethyllinalool, linalool oxide, geraniol, nerol, tetrahydrogeraniol, myrcenol, dihydromyrcenol, tetrahydromyrcenol, ocimenol, menthol, borneol, fenchyl alcohol, farnesol, nerolidol, cedrol, and terpineol. Among them, ethyllinalool is preferable from the viewpoint of enhancing the feeling of cleanliness and refreshingness by being blended with another fragrance.

Examples of aromatic alcohols include benzyl alcohol, styralyl alcohol, phenethyl alcohol, dimethyl phenyl ethyl carbinol, cinnamic alcohol, Phenyl Hexanol (Trade Name of Kao Corporation), Pamplefleur (Trade Name of IFF, 4-phenylpentanol), and Majantol (Trade Name of Symrise, 2,2-dimethyl-3-(3-methylphenyl)propanol).

Examples of phenols include anethole, guaiacol, eugenol, and isoeugenol.

Examples of aldehydes include aliphatic aldehyde, terpene aldehyde, and aromatic aldehyde as in the case of the aforementioned alcohols. All the aldehydes in which only the alcohol group of the fragrance component alcohols has been converted to aldehyde group are included in the examples of the fragrance components.

Examples of other aldehydes include Aldehyde C-6 (Trade Name of Kao Corporation, 1-hexanal), Aldehyde C-8 (Trade Name of Kao Corporation, 1-octanal), Aldehyde C-9 (Trade Name of Kao Corporation, 1-nonanal), Aldehyde C-10 (Trade Name of Kao Corporation, 1-decanal), Aldehyde C-11 Undecyl (Trade Name of Kao Corporation, undecanal), Aldehyde C-11 MOA (Trade Name of Symrise, 2-methyl decanal), Aldehyde C-111 LEN (Trade Name of Kao Corporation, 10-undecenal), Aldehyde C-12 LAURYL (Trade Name of Kao Corporation, 1-dodecanal), Aldehyde C-12 MNA (Trade Name of Kao Corporation, 2-methyl-undecanal), Floral Super (Trade Name of IFF, 4,8-dimethyl-4,9-decadienal), Pollenal II (Trade Name of Kao Corporation, 2-cyclohexyl-propanal), Myrac Aldehyde (Trade Name of IFF, 4(3)-(4-methyl-3-pentene-1-yl)-3-cyclohexene-1-carboxaldehyde), LYRAL (Trade Name of IFF, 4(3)-(4-hydroxy-4-methylpentyl)-3-cyclohexene-1-carboxaldehyde), Cetonal (Trade Name of Givaudan, trimethyl cyclohexen methylbutanal), Vernaldehyde (Trade Name of Givaudan, 1-methyl-4-(4-methylpentyl)-3-cyclohexenecarbaldehyde), Melozone (Trade Name of IFF, octahydro-4,7-methanoindenecarboxaldehyde), Scentenal (Trade Name of Firmenich, methoxydicyclopentadienecarboxaldehyde), Dupical (Trade Name of Givaudan, 4-tricyclodecylidenebutanal), Bergamal (Trade Name of IFF, 3,7-dimethyl-2-methylene-6-octenal), campholenic aldehyde, Bourgeonal (Trade Name of Givaudan, 3-(4-tert-butylphenyl)propanal), Cyclamen Aldehyde (Trade Name of Givaudan, 3-(4-isopropylphenyl)-2-methylpropionaldehyde), Floralozone (Trade Name of IFF, 3-(4-ethylphenyl)-2,2-dimethylpropionaldehyde), Suzaral (Trade Name of Takasago International Corporation, 3-(4-isobutylphenyl)-2-methylpropionaldehyde), Lilyall (Trade Name of Givaudan, 3-(4-t-butylphenyl)-2-methylpropionaldehyde), Amyl Cinnamic Aldehyde (Trade Name of Kao Corporation), Hexyl Cinnamic Aldehyde (Trade Name of Kao Corporation), Canthoxal (Trade Name of IFF, 2-methyl-3-(4-methoxyphenyl)propanal), vanillin, ethyl vanillin, Heliotropine (Trade Name of Takasago International Corporation, 3,4-methylenedioxybenzaldehyde), Helional (Trade Name of IFF, α-methyl-1,3-benzodioxole-5-propanal), and Triplal (Trade Name of IFF, 2,4-dimethyl-3-cyclohexene-1-carboxaldehyde). Bourgeonal, Lilyall, Hexyl Cinnamic Aldehyde, and Helional are preferable from the viewpoint of enhancing the feeling of cleanliness and refreshingness by being blended with another fragrance.

Examples of ketones include methyl heptenone, dimethyl octenone, 3-octanone, hexylcyclopentanone, dihydrojasmone, Veloutone (Trade Name of Firmenich, 2,2,5-trimethyl-5-pentylcyclopentanone), Nectaryl (Trade Name of Givaudan, 2-(2-(4-methyl-3-cyclohexen-1-yl)propyl)cyclopentanone), ionone, methylionone, γ-methylionone, damascone, α-damascone, δ-damascone, damascenone, Dynascone (Trade Name of Firmenich, 1-(5,5-dimethyl-1-cyclohexen-1-yl)-4-penten-1-one), irone, Cashmeran (Trade Name of IFF, 1,2,3,5,6,7-hexahydro-1,1,2,3,3-pentamethyl-4H-inden-4-one), Iso E Super (Trade Name of IFF, 1-(1,2,3,4,5,6,7,8-octahydro-2,3,8,8-tetramethyl-2-naphthalenyl)-ethan-1-one), Calone (Trade Name of Firmenich, 7-methyl-3,4-dihydro-2H-benzodioxepin-3-one), carvone, menthone, acetyl cedrene, isolongifolanone, nootkatone, benzyl acetone, raspberry ketone, benzophenone, Tonalid (Trade Name of PFW, 6-acetyl-1,1,2,4,4,7-hexamethyl tetrahydronaphthalene), β-methyl naphthyl ketone, muscone, Muscenone (Trade Name of Firmenich, 3-methyl-5-cyclopentadecen-1-one), civetone, Globanone (Trade Name of Symrise, 8-cyclohexadecenone), ethyl maltol, camphor, and Isodamascone (Trade Name of Symrise, 1-(2,4,4-trimethyl-2-cyclohexyl)-trans-2-butanone). Among them, α-damascone, δ-damascone, Iso E Super, or camphor is preferable from the viewpoint of enhancing the feeling of cleanliness and refreshingness by being blended with another fragrance.

Examples of acetals include Anthoxan (Trade Name of Kao Corporation), Boisambrene Forte (Trade Name of Kao Corporation), Troenan (Trade Name of Kao Corporation), Methyl Pamplemousse (Trade Name of Givaudan, 1,1-dimethoxy-2,2,5-trimethyl-4-hexene), citral dimethyl acetal, hydratropaldehyde dimethyl acetal, Verdoxan (Trade Name of Kao Corporation), acetaldehyde ethyl linalyl acetal, and Floropal (Trade Name of Symrise, 2,4,6-trimethyl-4-phenyl-1,3-dioxane).

Examples of ethers include Herbavert (Trade Name of Kao Corporation, 3,3,5-trimethylcyclohexyl ethyl ether), cedryl methyl ether, Ambroxan (Trade Name of Kao Corporation, [3aR-(3aα,5aβ,9aα,9bβ)]dodecahydro-3a,6,6,9a-tetramethyl naphto[2,1-b]furan), Ambrotech (Trade Name of Kao Corporation, dodecahydro-3a,6,6,9a-tetramethylnaphtho[2,1-b]furan), methyl isoeugenol, citronellyl ethyl ether, geranyl ethyl ether, 1,8-cineole, rose oxide, estragole, anethole, hinokitiol, diphenyl oxide, 6-naphthol methyl ether, 6-naphthol ethyl ether, and Galaxolide (Trade Name of IFF, 1,3,4,6,7,8-hexahydro-4,6,6,7,8,8-hexamethylcyclopenta-γ-2-benzopyran). Among them, Ambroxan is preferable from the viewpoint of enhancing the feeling of cleanliness and refreshingness by being blended with another fragrance.

Examples of esters to be used as a fragrance material include aliphatic carboxylic acid ester, aromatic carboxylic acid ester, and other carboxylic acid esters.

Examples of aliphatic carboxylic acids that form aliphatic carboxylic acid ester include linear and branched carboxylic acids having 1 to 18 carbon atoms. Among them, carboxylic acids having 1 to 6 carbon atoms such as formic acid, acetic acid, and propionic acid are important, and particularly acetic acid is important. Examples of aromatic carboxylic acids that form aromatic carboxylic acid ester include benzoic acid, anisic acid, phenylacetic acid, cinnamic acid, salicylic acid, and anthranilic acid. Examples of alcohols that form aliphatic and aromatic esters include linear and branched aliphatic alcohols having 1 to 5 carbon atoms and the above-mentioned fragrance component alcohols.

Examples of other carboxylic acid esters include Ethyl Safranate (Trade Name of Givaudan, ethyl dihydrocyclo geranate), Poirenate (Trade Name of Kao Corporation, ethyl 2-cyclohexyl propionate), Fruitate (Trade Name of Kao Corporation, ethyl tricyclo[5.2.1.0$^{2.6}$]decan-2-carboxylate), methyl jasmonate, MDJ (Trade Name of Kao Corporation, methyl dihydrojasmonate, methyl (2-pentyl-3-oxocyclopentyl)acetate), tricyclodecenyl propionate, and ethyl 3-methyl-3-phenylglycidate (Common Name; Aldehyde C-16). Among them, MDJ is preferable from the viewpoint of enhancing the feeling of cleanliness and refreshingness by being blended with another fragrance.

Examples of carbonates include Liffarome (Trade Name of IFF, cis-3-hexenyl methyl carbonate), Jasmacyclat (Trade Name of Kao Corporation), and Floramat (Trade Name of Kao Corporation). Among them, Liffarome is preferable from the viewpoint of enhancing the feeling of cleanliness and refreshingness by being blended with another fragrance.

Examples of lactones include γ-nonalactone, γ-decalactone, δ-decalactone, Jasmolactone (Trade Name of Firmenich, tetrahydro-6-(3-pentenyl)-2H-pyran-2-one), γ-undecalactone, coumarin, octahydrocoumarin, Florex (Trade Name of Firmenich, 6-ethylideneoctahydro-5,8-methano-2H-1-benzopyran-2-one), cyclopentadecanolide, Habanolide (Trade Name of Firmenich, 12(11)-oxacyclohexadecen-2-one), Ambrettolide (Trade Name of IFF, 10-octacycloheptadecen-2-one), and ethylene brassylate.

Examples of oximes include Buccoxime (Trade Name of Symrise, 1,5-dimethyl-bicyclo[3,2,1]octan-8-one oxime), Labienoxime (Trade Name of Givaudan, 2,4,4,7-tetramethyl-6,8-nonadiene-3-one oxime), and 5-methyl-3-heptanone oxime.

Examples of nitriles include dodecanenitrile, citronellyl nitrile, cuminyl nitrile, cinnamyl nitrile, and Peonile (Trade Name of Givaudan, 2-cyclohexylidene-2-phenylacetonitrile).

Examples of Schiff bases include Aurantiol (Trade Name of Givaudan, methyl N-(3,7-dimethyl-7-hydroxyoctylidene)-anthranilate), Ligantral (Trade Name of Givaudan, methyl (3,5-dimethyl-3-cyclohexene-1-yl)methyleneanthranilate), and methyl 2-[(2-methylundecylidene)amino]benzoate.

Examples of the natural essential oils and the natural extracts include orange, lemon, lime, bergamot, vanilla, mandarin, peppermint, spearmint, lavender, chamomile, rosemary, eucalyptus, sage, basil, rose, rockrose, geranium, jasmine, ylang ylang, anise, clove, ginger, nutmeg, cardamon, cedar, cypress, vetiver, patchouli, lemongrass, labdanum, galbanum, petitgrain, and olibanum. Among them, lime, bergamot, mandarin, or spearmint is preferable from the viewpoint of enhancing the feeling of cleanliness and refreshingness by being blended with another fragrance.

The amount of these other fragrances to be contained can be selected suitably depending on, for example, the type of the blended fragrance as well as the type and intensity of intended odor. However, in the fragrance composition, the amount of each of them contained therein is preferably 0.0001 to 99.99 mass %, more preferably 0.001 to 80 mass %. In the fragrance composition, the total amount of them contained therein is preferably 5 to 99.99 mass %, more preferably 50 to 99.9 mass %.

The fragrance composition of the present invention can contain an oil, which itself has no odor, to be used as a base that allows 13-methyl-9-cyclopentadecen-15-olide of the present invention and other fragrance materials to be contained therein. Such an oil allows a fragrance component to be mixed uniformly, to be easily mixed into a product, and to be easily provided with a suitable intensity of fragrance. Examples of the oil include polyhydric alcohols such as ethylene glycol, propylene glycol, butylene glycol, and dipropylene glycol, esters such as isopropyl myristate, dibutyl adipate, and diethyl sebacate, hydrocarbons such as liquid paraffin and squalane, and surfactants such as polyoxyethylene alkyl ether and sorbitan fatty acid ester. Furthermore, the fragrance composition of the present invention can contain a base, which itself has an odor, as a base that allows 13-methyl-9-cyclopentadecen-15-olide of the present invention and other fragrance materials to be contained therein. Examples of such a base include an apple base, a cassis base, a melon base, and a banana base. The apple base can contain, for example, pearlide, Aldehyde C-14 Peach, o-t-butyl cyclohexyl acetate, and prenyl acetate. The cassis base can contain, for example, Lyral, methyl dihydrojasmonate, Triplal, and beta-pinene.

Among them, from the viewpoint of the solubility of all the fragrance components, the oil is preferably polyhydric alcohol or ester, more preferably dipropylene glycol or isopropyl myristate. The amount of such an oil to be contained in the fragrance composition is preferably 0.01 to 95 mass %, more preferably 1 to 90 mass %, and further preferably 4 to 70 mass %.

The fragrance composition of the present invention also provides effects of further emphasizing the top note and enhancing the feeling of cleanliness and refreshingness in addition to the odor of 13-methyl-9-cyclopentadecen-15-olide. Such a fragrance composition can be used suitably to provide fragrances for cleanser compositions, fabric treatment compositions, cosmetics, etc.

[Use as Fragrance Component]

The fragrance composition containing 13-methyl-9-cyclopentadecen-15-olide of the present invention can be used, as a fragrance component for various types of products, as a blended fragrance with a preferable fragrance note that has an odor with a tone of musk and a side note of woody tone, that is excellent in fragrance retention, and that emphasizes the top note and enhances the feeling of cleanliness and refreshingness by being blended with another fragrance. Therefore, the present invention provides a method of using 13-methyl-9-cyclopentadecen-15-olide as a fragrance component, preferably a method of using 13-methyl-9-cyclopentadecen-15-olide as a fragrance component for a fragrance composition, a cleanser composition, a fabric treatment composition, or a cosmetic. For the method of using said compound, it can be contained, alone or in combination with other components, in the bases of toiletry products such as soaps, cosmetics, hair cosmetics, detergents, softeners, spray products, air fresheners, perfumes, and bath agents.

Particularly, it is preferable that 13-methyl-9-cyclopentadecen-15-olide of the present invention be used for applications in which a fragrance note that emphasizes the top note and has enhanced fragrance retention, feeling of cleanliness, and refreshingness is used preferably. Therefore, 13-methyl-9-cyclopentadecen-15-olide is used preferably for cleanser compositions and fabric treatment compositions, more preferably for cleanser compositions.

Accordingly, the present invention also provides a cleanser composition, a fabric treatment composition, and a cosmetic that each contain a fragrance composition of the present invention.

The cleanser composition of the present invention is preferably a cleanser composition for hard surfaces, a cleanser composition for clothing, or a body cleanser composition, more preferably a cleanser composition for hard surfaces.

Examples of the cleanser composition for hard surfaces include an all purpose cleaner and a cleanser composition for tableware.

Examples of the body cleanser composition include a skin cleanser composition and a hair cleanser composition. It is preferably a hair cleanser composition.

The fabric treatment composition is preferably a softener composition.

The cosmetic of the present invention is preferably a perfume.

It is preferable that the cleanser composition of the present invention contain an anionic surfactant in addition to 13-methyl-9-cyclopentadecen-15-olide of the present invention. Furthermore, a nonionic surfactant, a pH adjuster, a viscosity modifier, a solvent, an oil, a preservative, water, etc. can be blended thereinto.

It is preferable that the softener composition of the present invention contain a cationic surfactant in addition to 13-methyl-9-cyclopentadecen-15-olide of the present invention. Furthermore, a pH adjuster, a solvent, an oil, a preservative, water, etc. can be blended thereinto.

In the perfume of the present invention, a solvent, water, etc. can be blended thereinto in addition to 13-methyl-9-cyclopentadecen-15-olide of the present invention.

With respect to the above-described embodiment, the present invention further discloses 13-methyl-9-cyclopentadecen-15-olide and a method of producing 13-methyl-9-cyclopentadecen-15-olide.

<1> 13-Methyl-9-cyclopentadecen-15-olide.

<2> 13-Methyl-9-cyclopentadecen-15-olide according to the item <1>, wherein 13-methyl-9-cyclopentadecen-15-olide is (S)-13-methyl-9-cyclopentadecen-15-olide.

<3> 13-Methyl-9-cyclopentadecen-15-olide according to the item <1>, wherein 13-methyl-9-cyclopentadecen-15-olide is (R)-13-methyl-9-cyclopentadecen-15-olide.

<4> 13-Methyl-9-cyclopentadecen-15-olide according to the item <1>, wherein 13-methyl-9-cyclopentadecen-15-olide is a mixture of (S)-13-methyl-9-cyclopentadecen-15-olide and (R)-13-methyl-9-cyclopentadecen-15-olide.

<5> 13-Methyl-9-cyclopentadecen-15-olide according to the item <4>, wherein the excess rate of (S)-13-methyl-9-cyclopentadecen-15-olide is preferably 0% or higher, more preferably at least 50%, further preferably at least 95%, and still further preferably 100%.

<6> A fragrance composition, containing 13-methyl-9-cyclopentadecen-15-olide according to any one of the items <1> to <5>.

<7> The fragrance composition according to the item <6>, wherein the amount of 13-methyl-9-cyclopentadecen-15-olide contained in the fragrance composition is preferably 0.01 to 99 mass %, more preferably 0.1 to 15 mass %, and further preferably 0.3 to 3 mass %.

<8> The fragrance composition according to the item <7>, further containing a fragrance in addition to 13-methyl-9-cyclopentadecen-15-olide.

<9> The fragrance composition according to the item <8>, wherein the fragrance contained in addition to 13-methyl-9-cyclopentadecen-15-olide contains at least one selected from hydrocarbons, alcohols, phenols, aldehydes, ketones, acetals, ethers, esters, carbonates, lactones, oximes, nitriles, Schiff bases, amides, natural essential oils, and natural extracts.

<10> A cleanser composition containing a fragrance composition according to any one of the items <6> to <9>.

<11> A fabric treatment composition containing a fragrance composition according to any one of the items <6> to <9>.

<12> A cosmetic containing a fragrance composition according to any one of the items <6> to <9>.

<13> A method of using 13-methyl-9-cyclopentadecen-15-olide according to any one of the items <1> to <5> as a fragrance component for a fragrance composition, a cleanser composition, a softener composition, or a cosmetic.

<14> A method of producing 13-methyl-9-cyclopentadecen-15-olide, including a step of cyclizing 3,7-dimethyl-6-octenyl-9-decenoate by a metathesis reaction.

<15> The method of producing 13-methyl-9-cyclopentadecen-15-olide according to the item <14>, wherein the metathesis reaction is carried out using preferably a rhenium catalyst, a tungsten catalyst, a molybdenum catalyst, or a ruthenium catalyst, more preferably a ruthenium catalyst, further preferably a ruthenium catalyst with a carbene ligand, and still further preferably a Grubbs catalyst represented by Formula (X).

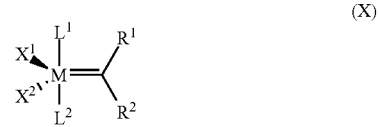

In Formula (X), M is Ru. $X^1$ and $X^2$ each are an anionic ligand, preferably halogen, and more preferably chlorine (Cl). $X^1$ and $X^2$ may be identical to or different from each other. $R^1$ and $R^2$ each are H or a hydrocarbon group having 1 to 20 carbon atoms that may have a substituent. $R^1$ and $R^2$ may be identical to or different from each other. Alternatively, $R^1$ and $R^2$ may be combined together to form a ring structure. $L^1$ and L² each are a neutral ligand. L¹ and L² may be identical to or different from each other. Alternatively, either one of L¹ and L², either one of R¹ and R², and M may be combined together to form a ring structure.

<16> A method of producing 13-methyl-9-cyclopentadecen-15-olide according to the item <15> that satisfies the following conditions. In Formula (X), the ligand of either one of L¹ and L² is preferably phosphine or N-heterocyclic carbene from the viewpoint of increasing the yield. The phosphine is preferably trialkylphosphine, more preferably tricyclohexylphosphine. The N-heterocyclic carbene is preferably a pyridinium group or a group represented by Formula (Y), more preferably a group represented by Formula (Y).

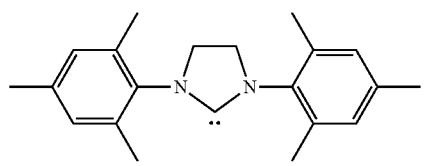

(Y)

R¹ and R² may be combined together to form a ring or may not be combined together to form a ring. From the viewpoint of increasing the yield, it is preferable that R¹ and R² be combined together to form a ring.

When R¹ and R² are combined together to form a ring structure, the ring structure is preferably 3-phenyl-1H-indene-1-ylidene from the viewpoint of increasing the yield.

<17> The method of producing 13-methyl-9-cyclopentadecen-15-olide according to the item <15>, wherein the Grubbs catalyst represented by Formula (X) is preferably a Grubbs catalysts represented by one of Formulae (X1) to (X9) below, more preferably a Grubbs catalysts represented by one of Formulae (X1) to (X5) and (X9), and further preferably a Grubbs catalysts represented by Formula (X9). In the formulae, PCy₃ denotes tricyclohexylphosphine, Mes denotes a 2,4,6-trimethylphenyl group, and ⁱPr denotes an isopropyl group.

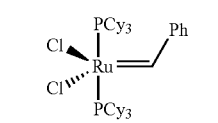

(X1)

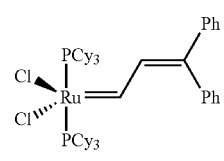

(X2)

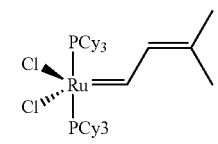

(X3)

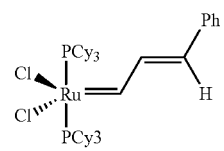

(X4)

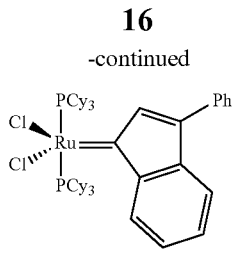

(X5)

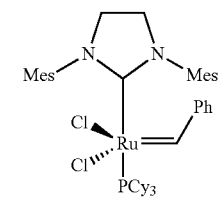

(X6)

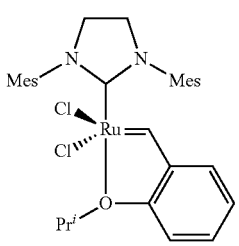

(X7)

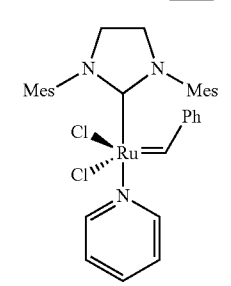

(X8)

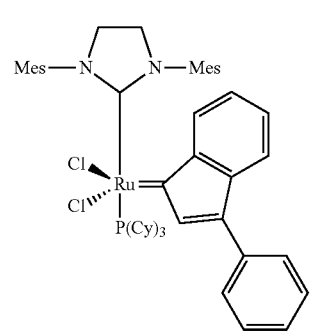

(X9)

<18> The method of producing 13-methyl-9-cyclopentadecen-15-olide according to any one of the items <14> to <17>, wherein the method includes a step of obtaining 3,7-dimethyl-6-octenyl-9-decenoate by dehydration condensation of 3,7-dimethyl-6-octene-1-ol and 9-decenoic acid.

<19> The method of producing 13-methyl-9-cyclopentadecen-15-olide according to the item <18>, wherein the dehydration condensation is carried out preferably by a method of azeotropic dehydration carried out in the presence of acid catalyst using a solvent such as toluene or a method of stirring in the presence of a dehydrating agent, and more preferably by a method of stirring in the presence of a dehydrating agent.

<20> The method of producing 13-methyl-9-cyclopentadecen-15-olide according to the item <19>, wherein the dehydrating agent is preferably carbodiimides, more preferably N,N'-dicyclohexylcarbodiimide or 1-ethyl-3-(3-dimethylaminopropyl)carbodiimide hydrochloride, and further preferably 1-ethyl-3-(3-dimethylaminopropyl)carbodiimide hydrochloride.

<21> The method of producing 13-methyl-9-cyclopentadecen-15-olide according to any one of the items <18> to <20>, wherein the dehydration condensation is carried out in the presence of preferably a reaction accelerator, more preferably tertiary amines, further preferably pyridines, and still further preferably N,N'-dimethylaminopyridine.

EXAMPLES

The following examples further describe and demonstrate embodiments of the present invention. The examples are given solely for the purpose of illustration and are not to be construed as limitations of the present invention.

The details of the measurement methods carried out in the following examples and comparative examples are described together below.

The details of the measurement methods carried out in the following production examples are described together below.

[Reaction Yield]

The reaction yield described in the following production examples was determined by an internal standard method of gas chromatography (GC) quantitative analysis.

<Apparatus and Analytical Conditions for Gas Chromatography>

GC Apparatus: HP6850, manufactured by HEWLETT PACKARD

Column: DB-1 (Inner Diameter: 0.25 mm, Length: 30 m, and Film Thickness: 0.25 μm), manufactured by J&W Carrier Gas: He, 1.5 mL/min Injection Condition: 300° C., Split Ratio: 1/100

Detection Condition: FID System, 300° C.

Column Temperature Condition: Raised from 80° C. to 300° C. at 10° C./min then maintained at 300° C. for 10 minutes.

Internal Standard Compound: n⁻ tridecane

[Compound Identification]

Each compound obtained in the following production examples was identified by spectrum analyses using a nuclear magnetic resonance spectrum (Mercury 400, manufactured by Varian) ($^1$H-NMR, $^{13}$C-NMR) and a gas chromatography mass spectrometer (GC-MS) (GC-2010, manufactured by Shimadzu Corporation).

<GC-MS Apparatus and Analytical Conditions>

GC-MS Apparatus: GC2010, manufactured by Shimadzu Corporation

Column: GLC RESTEK (Inner Diameter: 0.25 mm, Length: 25 m, and Film Thickness: 0.25 μm), manufactured by Shimadzu Corporation Carrier Gas: He, 1.82 mL/min Injection Condition: 280° C., Split Ratio: 1/50

Detection Condition: GCMS-PQ2010 Plus, 280° C.

Column Temperature Condition: Raised from 80° C. to 280° C. at 5° C./min then maintained at 280° C. for 10 minutes.

Mass Range: Low 70, High 450

[Odor Evaluation]

Two experts who had an experience of blending odors and evaluating fragrances determined the fragrance note and the intensity by a smelling strip method. About 5 mm of the end of each smelling strip (fragrance test paper with a width of 6 mm and a length of 150 mm) was immersed in a sample and thereby evaluation was performed.

With respect to the odor, fragrances that are sensed mainly (main odors) were listed from the strongest to the weakest and further fragrances that are sensed secondarily (secondary odors) were noted.

The odor intensity was indicated by the result of the evaluation, with 0 denoting odorless and 5 denoting very strong (a six grades odor intensity measurement method).

[Evaluation of Fragrance Retention]

As in the case of the above-mentioned smelling strip method, a strip was immersed in a sample and then was left in a 5 m³ windless room at 25° C. It was evaluated every 7 days and the number shown is the number of weeks that passed until the odor intensity of the main odor became zero. The larger the number of weeks, the better the fragrance retention. Habanolide (manufactured by Firmenich) was evaluated by this method and the number of weeks was two.

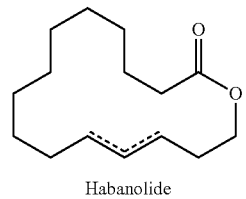

Habanolide

Production Example 1

Production of 3,7-Dimethyl-6-Octenyl-9-Decenoate

In a 100 mL flask, 3,7-dimethyl-6-octene-1-ol ((±)-citronellol, manufactured by Wako Pure Chemical Industries, Ltd., Purity: 90%, 2.1 g, 12.1 mmol) and 9-decenoic acid (2.4 g, 14.0 mmol) were placed and then were dissolved in dichloromethane (25 mL). Subsequently, 1-ethyl-3-(3-dimethylaminopropyl)carbodiimide hydrochloride (3.2 g, 16.5 mmol, 136 mol % with respect to 3,7-dimethyl-6-octene-1-ol and 118 mol % with respect to 9-decenoic acid) and N,N'-dimethylaminopyridine (146 mg, 1.2 mmol, 10 mol % with respect to citronellol) were added to the flask. This was allowed to react under a nitrogen gas stream at room temperature for five hours. An ammonium chloride aqueous solution was added to a reaction solution obtained after the reaction was completed, which then was stirred. Thereafter, it was subjected to settled separation and thereby an aqueous layer was extracted and an oil layer was washed with saturated saline. Then sodium sulfate was added to the oil layer to dehydrate to dryness. After filtration thereof, dichloromethane was evaporated to dryness from the oil layer and thereby 3,7-dimethyl-6-octenyl-9-decenoate (3.7 g, 12.0 mmol, the yield in terms of 3,7-dimethyl-6-octene-1-ol: 100%) was obtained.

The measurement results of respective spectrum analyses of 3,7-dimethyl-6-octenyl-9-decenoate are shown below.

(1) $^1$H-NMR (CDCl$_3$, 400 MHz); δ (ppm): 0.91 (d, 3H, J=6.4 Hz), 1.18 (m, 1H), 1.30-1.47 (m, 10H), 1.50-1.70 (m, 4H), 1.60 (s, 3H), 1.68 (s, 3H), 1.92-2.05 (m, 4H), 2.28 (t, 2H, J=7.6 Hz), 4.09 (m, 2H), 4.92 (d, 1H, J=10.0 Hz), 4.98 (d, 1H, J=17.2 Hz), 5.08 (t, 1H, J=7.0 Hz), 5.79 (m, 1H).

(2) $^{13}$C-NMR (CDCl$_3$, 100 MHz); δ (ppm): 174.1, 139.3, 131.5, 124.8, 114.4, 63.1, 37.4, 35.9, 34.8, 34.2, 29.9, 29.5, 29.5, 29.4, 29.3, 26.2, 25.8, 25.4, 19.9, 18.1.

(3) MS (CI) m/Z: 309 (M⁺), 171, 139, 83, 71

Example 1

Production of 13-Methyl-9-Cyclopentadecen-15-Olide

In a 2 L three-necked flask, 3,7-dimethyl-6-octenyl-9-decenoate (0.85 g, 2.8 mmol) obtained in Production Example 1, dichloromethane (650 mL), and a metathesis catalyst (Umicore M2 (Trade Name), manufactured by Umicore Japan KK, 74 mg, 0.078 mmol, and 3 mol % with respect to the substrate) represented by the formula below were placed, which then was heated to reflux under a nitrogen gas stream at 50° C. for six hours. The reaction solution obtained after the reaction was completed was subjected to gas chromatography quantitative analysis and was found to contain 13-methyl-9-cyclopentadecen-15-olide (0.6 g, 2.4 mmol, Yield: 86%).

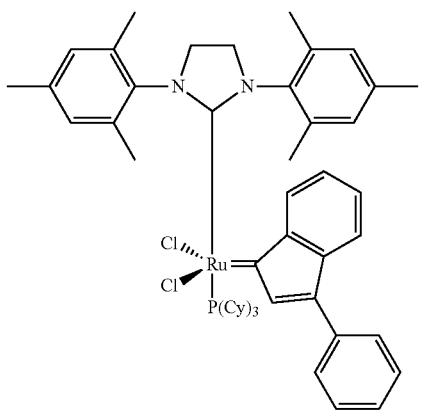

Dichloromethane was evaporated to dryness from the reaction solution and the residue was purified by column chromatography (Developing Solvent: n-hexane:ethyl acetate=99:1). Thus, 0.4 g (1.6 mmol) of 13-methyl-9-cyclopentadecen-15-olide was obtained. 13-Methyl-9-cyclopentadecen-15-olide had a purity of 95.7%. The S-form excess rate was 0%.

The measurement results of respective spectrum analyses of 13-methyl-9-cyclopentadecen-15-olide are shown below.

(1) $^1$H-NMR (CDCl$_3$, 400 MHz); δ (ppm): 0.84 (d, 3H, J=6.4 Hz), 1.12-1.41 (m, 10H), 1.47 (m, 1H), 1.58-1.73 (m, 4H), 1.96-2.16 (m, 4H), 2.31 (m, 2H), 4.09 (m, 1H), 4.19 (s, 1H), 5.30 (m, 2H).

(2) $^{13}$C-NMR (CDCl$_3$, 100 MHz); δ (ppm): 173.9, 131.1, 130.6, 62.0, 36.7, 36.7, 34.9, 31.5, 29.8, 29.0, 27.8, 27.4, 27.1, 26.7, 25.0, 17.5.

(3) MS (CI) m/Z: 253 (M$^+$), 235

(4) Odor: Main Odor: Refreshing Musk; and Secondary Odor: Woody (5) Odor Intensity: 3

(6) Fragrance Retention: 4 Weeks

Production Example 2

Production of (S)-3,7-Dimethyl-6-Octenyl-9-Decenoate

Production was carried out in the same manner as in Production Example 1 except that (S)-(−)-citronellol (manufactured by SIGMA-ALDRICH, (S)-(−)-3,7-dimethyl-6-octene-1-ol) was used instead of (±)-citronellol. Thus (S)-3,7-dimethyl-6-octenyl-9-decenoate was obtained.

Example 2

Production of (S)-13-Methyl-9-Cyclopentadecen-15-Olide

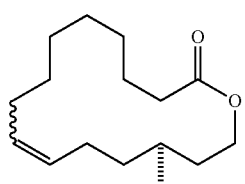

(S)-13-methyl-9-cyclo pentadecen-15-olide

Production was carried out in the same manner as in Example 1 except for using the (S)-3,7-dimethyl-6-octenyl-9-decenoate obtained in Production Example 2. Thus (S)-13-methyl-9-cyclopentadecen-15-olide was obtained. (S)-13-Methyl-9-cyclopentadecen-15-olide thus obtained had a purity of 95.7%. The S-form excess rate was 100%.

The measurement results of respective spectrum analyses of (S)-13-methyl-9-cyclopentadecen-15-olide are shown below.

(1) $^1$H-NMR (CDCl$_3$, 400 MHz); δ (ppm): 0.84 (d, 3H, J=6.4 Hz), 1.12-1.41 (m, 10H), 1.47 (m, 1H), 1.58-1.73 (m, 4H), 1.96-2.16 (m, 4H), 2.31 (m, 2H), 4.09 (m, 1H), 4.19 (s, 1H), 5.30 (m, 2H).

(2) $^{13}$C-NMR (CDCl$_3$, 100 MHz); δ (ppm): 173.9, 131.1, 130.6, 62.0, 36.7, 36.7, 34.9, 31.5, 29.8, 29.0, 27.8, 27.4, 27.1, 26.7, 25.0, 17.5.

(3) MS (CI) m/Z: 253 (M$^+$), 235

(4) Odor: Main Odor: Deep Refreshing Musk with Diffusibility; and Secondary Odor: Woody (5) Odor Intensity: 4

Production Example 3

Production of (R)-3,7-Dimethyl-6-Octenyl-9-Decenoate

Production was carried out in the same manner as in Production Example 1 except that (R)-(+)-citronellol (manufactured by SIGMA-ALDRICH, (R)-(+)-3,7-dimethyl-6-octene-1-ol) was used instead of (±)-citronellol. Thus (R)-3,7-dimethyl-6-octenyl-9-decenoate was obtained.

Example 3

Production of (R)-13-Methyl-9-Cyclopentadecen-15-Olide

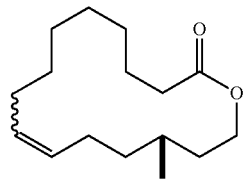

(R)-13-methyl-9-cyclo
pentadecen-15-olide

Production was carried out in the same manner as in Example 1 except for using the (R)-3,7-dimethyl-6-octenyl-9-decenoate obtained in Production Example 3. Thus (R)-13-methyl-9-cyclopentadecen-15-olide was obtained. (R)-13-Methyl-9-cyclopentadecen-15-olide thus obtained had a purity of 98.1%. The R-form excess rate was 100%.

The measurement results of respective spectrum analyses of (R)-13-methyl-9-cyclopentadecen-15-olide are shown below.

(1) $^1$H-NMR (CDCl$_3$, 400 MHz); δ (ppm): 0.84 (d, 3H, J=6.4 Hz), 1.12-1.41 (m, 10H), 1.47 (m, 1H), 1.58-1.73 (m, 4H), 1.96-2.16 (m, 4H), 2.31 (m, 2H), 4.09 (m, 1H), 4.19 (s, 1H), 5.30 (m, 2H).

(2) $^{13}$C-NMR (CDCl$_3$, 100 MHz); δ (ppm): 173.9, 131.1, 130.6, 62.0, 36.7, 36.7, 34.9, 31.5, 29.8, 29.0, 27.8, 27.4, 27.1, 26.7, 25.0, 17.5.

(3) MS (CI) m/Z: 253 (M$^+$), 235

Comparative Example 1

Production of 13-Methyl-15-Cyclopentadecanolide

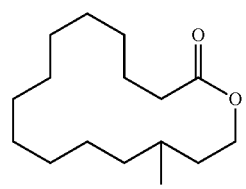

13-Methyl-15-
cyclopentadecanolide

In a 50 mL two-necked flask, 13-methyl-9-cyclopentadecen-15-olide (Purity: 95.7%, 465 mg, 1.7 mmol) obtained in Example 1 was placed and was dissolved in 10 ml of methanol. Then 5% active carbon-supported palladium catalyst (23 mg) was added to the solution thus obtained, which then was hydrogenated at room temperature under a hydrogen pressure of 0.1 MPa for one hour. After the catalyst was filtered to be removed, the solvent was removed under reduced pressure from the reaction solution thus obtained. Thereafter the concentrate thus obtained was subjected to distillation purification and thereby 416 mg of 13-methyl-15-cyclopentadecanolide (Purity: 95.5%) was obtained.

The measurement results of respective spectrum analyses of the 13-methyl-15-cyclopentadecanolide are shown below.

(1) $^1$H-NMR (CDCl$_3$, 400 MHz); δ (ppm): 0.90 (d, 3H, J=6.4 Hz), 1.13 (m, 1H), 1.24-1.45 (m, 18H), 1.59-1.71 (m, 4H), 2.32 (m, 2H), 4.08 (m, 1H), 4.23 (m, 1H).

(2) $^{13}$C-NMR (CDCl$_3$, 100 MHz); δ (ppm): 174.0, 61.9, 35.4, 34.6, 34.3, 27.8, 27.3, 26.7, 26.5, 26.4, 26.2, 26.0, 25.0, 24.6, 19.6, 19.5.

(3) MS (CI) m/Z: 255 (M$^+$)

(4) Odor: Main Odor: Nitromusk-like Musk; and Secondary Odor: None (5) Odor Intensity: 3

(6) Fragrance Retention: 2 Weeks

Example 4 and Comparative Examples 2 to 3

Blended Fragrance for Cleanser (Fragrance Composition)

Using 13-methyl-9-cyclopentadecen-15-olide obtained in Example 1, Habanolide, and Pentalide (cyclopentadecanolide), fragrances of Example 4, Comparative Examples 2, and Comparative Example 3 were blended in such a manner as to have blended compositions indicated in Table 1, respectively. Thus blended fragrances (fragrance compositions) were prepared.

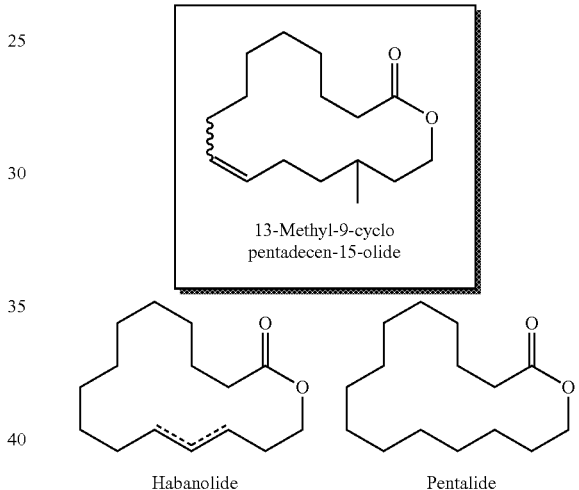

TABLE 1

| Components | Ex. 4 | C. Ex. 2 | C. Ex. 3 |
|---|---|---|---|
| Habanolide | — | 75.0 | — |
| Pentalide | — | — | 75.0 |
| 13-Methyl-9-Cyclopentadecen-15-Olide | 75.0 | — | — |
| α-Damascone | 1.0 | 1.0 | 1.0 |
| Amber Core | 75.0 | 75.0 | 75.0 |
| Ambroxan | 1.5 | 1.5 | 1.5 |
| Benzyl Salicylate | 25.0 | 25.0 | 25.0 |
| Bergamot Oil BGF CP | 50.0 | 50.0 | 50.0 |
| Bourgeonal | 7.5 | 7.5 | 7.5 |
| Cassis Base (KAO) | 20.0 | 20.0 | 20.0 |
| Dipropylene Glycol | 42.2 | 42.2 | 42.2 |
| δ-Damascone | 1.5 | 1.5 | 1.5 |
| Ethyllinalool | 30.0 | 30.0 | 30.0 |
| Green Apple Base (KAO) | 25.0 | 25.0 | 25.0 |
| Helional | 15.0 | 15.0 | 15.0 |
| Hexyl Acetate | 4.0 | 4.0 | 4.0 |
| Hexyl Cinnamic Aldehyde | 50.0 | 50.0 | 50.0 |
| Iso E Super | 150.0 | 150.0 | 150.0 |
| Liffarome | 1.5 | 1.5 | 1.5 |
| Lilyall | 60.0 | 60.0 | 60.0 |
| Lime Oil | 5.0 | 5.0 | 5.0 |
| Lyral | 40.0 | 40.0 | 40.0 |
| MDJ | 300.0 | 300.0 | 300.0 |

TABLE 1-continued

| Components | Ex. 4 | C. Ex. 2 | C. Ex. 3 |
|---|---|---|---|
| Mandarin Oil | 20.0 | 20.0 | 20.0 |
| Spearmint MWS RECT. | 0.8 | 0.8 | 0.8 |
| Total | 1000.0 | 1000.0 | 1000.0 |

The evaluations were performed in the same manner as in the aforementioned odor evaluation. Compared to the fragrance compositions of Comparative Examples 2 and 3, the fragrance composition of Example 4 lifted the top note (citrus, green, and fruitiness) and enhanced the feeling of cleanliness and refreshingness.

Example 5 and Comparative Examples 4 and 5

Cleanser Composition for Clothing

To a non-fragranced liquid cleanser for clothing having the composition indicated in Table 2, each of the fragrance compositions obtained in Example 4 and Comparative Examples 2 and 3 was added in such a manner as to be 0.6 mass %. Thus, cleanser compositions of Example 5 and Comparative Examples 4 and 5 were prepared respectively. With respect to these cleanser compositions, the following odor evaluation was performed.

[Odor Evaluation]

One expert who had an experience of seven years of blending odors and evaluating fragrances evaluated odors in the following manner. In a 100 ml glass bottle, 50 ml of each of the cleanser compositions of the example and the comparative examples was placed, which then was sealed and allowed to stand at 25° C. for 24 hours. Thereafter the expert evaluated the odor at the mouth of the bottle when it was opened.

TABLE 2

| Non-fragranced liquid cleanser for clothing | Blended Amount (mass %) |
|---|---|
| 70% Sodium polyoxyethylene(2) alkyl(C10-16) ether sulfate [1] | 9.0 |
| Polyethoxyethylene (10) lauryl ether [2] | 6.3 |
| Linear fatty acid [3] | 2.8 |
| 50% Citric acid | 5.9 |
| 48% Sodium hydroxide | 4.5 |
| Ethanol | 1.0 |
| Ion exchanged water | Remainder |
| pH | 7.3 |

[1] Trade Name of Kao Corporation: Emal 270J
[2] Trade Name of Kao Corporation: Emulgen 110L
[3] Trade Name of Kao Corporation: Lunac L-55

Comparative Example 4 had a clean musk odor and Comparative Example 5 had an odor provided with mild sweetness. On the other hand, the cleanser composition of Example 5 had emphasized green fruitiness and it was fresher and had enhanced feeling of cleanliness and refreshingness as compared to the cleanser compositions of the comparative examples.

Since 13-methyl-9-cyclopentadecen-15-olide of the present invention has an odor with a tone of musk and a side note of woody tone that are useful as fragrances and is excellent in fragrance retention, it can be used as a fragrance material. Furthermore, 13-methyl-9-cyclopentadecen-15-olide of the present invention can have an emphasized top note and enhanced feeling of cleanliness and refreshingness by being blended with another fragrance.

Thus, fragrance compositions containing 13-methyl-9-cyclopentadecen-15-olide of the present invention can be used as fragrance components for cleanser compositions, softener compositions, etc.

The invention may be embodied in other forms without departing from the spirit or essential characteristics thereof. The embodiments disclosed in this application are to be considered in all respects as illustrative and not limiting. The scope of the invention is indicated by the appended claims rather than by the foregoing description, and all changes which come within the meaning and range of equivalency of the claims are intended to be embraced therein.

What is claimed is:

1. 13-Methyl-9-cyclopentadecen-15-olide.

2. 13-Methyl-9-cyclopentadecen-15-olide according to claim 1, wherein it is (S)-13-methyl-9-cyclopentadecen-15-olide.

3. 13-Methyl-9-cyclopentadecen-15-olide according to claim 1, wherein it is (R)-13-methyl-9-cyclopentadecen-15-olide.

4. 13-Methyl-9-cyclopentadecen-15-olide according to claim 1, wherein it is a mixture of (S)-13-methyl-9-cyclopentadecen-15-olide and (R)-13-methyl-9-cyclopentadecen-15-olide.

5. 13-Methyl-9-cyclopentadecen-15-olide according to claim 4, wherein the excess rate of (S)-13-methyl-9-cyclopentadecen-15-olide is at least 50%.

6. 13-Methyl-9-cyclopentadecen-15-olide according to claim 4, wherein the excess rate of (S)-13-methyl-9-cyclopentadecen-15-olide is at least 95%.

7. A fragrance composition comprising 13-methyl-9-cyclopentadecen-15-olide according to claim 1.

8. The fragrance composition according to claim 7, wherein the amount of 13-methyl-9-cyclopentadecen-15-olide contained in the fragrance composition is 0.01 to 99 mass %.

9. The fragrance composition according to claim 7, wherein the amount of 13-methyl-9-cyclopentadecen-15-olide contained in the fragrance composition is 0.1 to 15 mass %.

10. The fragrance composition according to claim 7, wherein the amount of 13-methyl-9-cyclopentadecen-15-olide contained in the fragrance composition is 0.3 to 3 mass %.

11. The fragrance composition according to claim 7, further comprising a fragrance in addition to 13-methyl-9-cyclopentadecen-15-olide.

12. The fragrance composition according to claim 11, wherein the fragrance present in addition to 13-methyl-9-cyclopentadecen-15-olide comprises at least one member selected from the group consisting of a hydrocarbon, an alcohol, a phenol, an aldehyde, a ketone, an acetal, an ether, an ester, a carbonate, a lactone, an oxime, a nitrile, a Schiff base, an amide, a natural essential oil, and a natural extract.

13. A fabric treatment composition comprising the fragrance composition according to claim 7.

14. A cleanser composition comprising 13-methyl-9-cyclopentadecen-15-olide according to claim 1.

15. The cleanser composition according to claim 14, wherein it is a cleanser composition for clothing.

16. The cleaner composition according to claim 14, further comprising an anionic surfactant.

17. A method of making a composition selected from the group consisting of a fragrance composition, a cleanser composition, a softener composition and a cosmetic composition, comprising adding 13-methyl-9-cyclopentadecen-15-olide to said composition.

* * * * *

UNITED STATES PATENT AND TRADEMARK OFFICE
CERTIFICATE OF CORRECTION

PATENT NO. : 9,217,123 B2
APPLICATION NO. : 14/219486
DATED : December 22, 2015
INVENTOR(S) : Yuki Nakazawa et al.

Page 1 of 1

It is certified that error appears in the above-identified patent and that said Letters Patent is hereby corrected as shown below:

On the title page, Item (71) and Item (73), the Applicant's and the Assignee's information is incorrect. Item (71) and Item (73) should read:

--(71) Applicant: Kao Corporation, Tokyo, (JP)--

--(73) Assignee: Kao Corporation, Tokyo, (JP)--

Signed and Sealed this
Fifth Day of July, 2016

Michelle K. Lee
*Director of the United States Patent and Trademark Office*